United States Patent [19]
van Nijnatten et al.

[11] Patent Number: 6,051,215
[45] Date of Patent: Apr. 18, 2000

[54] NITRATE DEODORANT COMPOSITION

[75] Inventors: Hans A. M. van Nijnatten, Breda; Frans A. van der Pluijm, Dongen, both of Netherlands

[73] Assignee: Thetford Corporation, Ann Arbor, Mich.

[21] Appl. No.: 09/019,001

[22] Filed: Feb. 5, 1998

[51] Int. Cl.[7] .................................................. C01B 21/42
[52] U.S. Cl. ........................................ 424/76.1; 423/390
[58] Field of Search ................................ 424/76.1, 76.8, 424/76.9, 402, 404; 423/390; 422/5, 6

[56] References Cited

U.S. PATENT DOCUMENTS

| | | | |
|---|---|---|---|
| 4,205,054 | 5/1980 | Sugahara et al. ..................... | 423/390 |
| 5,312,594 | 5/1994 | Heller et al. ........................... | 422/106 |
| 5,376,166 | 12/1994 | Hoffmann et al. ..................... | 95/216 |

FOREIGN PATENT DOCUMENTS

| | | |
|---|---|---|
| 0559272 | 2/1993 | European Pat. Off. . |
| 0 559 272 A1 | 9/1993 | European Pat. Off. . |

*Primary Examiner*—Jose' G. Dees
*Assistant Examiner*—Kathryne E. Shelborne
*Attorney, Agent, or Firm*—Harness, Dickey & Pierce, P.L.C.

[57] ABSTRACT

A nitrate deodorant composition is provided which may be used in sewage-related settings such as waste holding tanks. The composition of the present invention comprises sodium, ammonium, potassium, and/or calcium nitrate beads wetted with a fragrance and dusted with a drying agent to produce dry, free flowing granules.

9 Claims, 1 Drawing Sheet

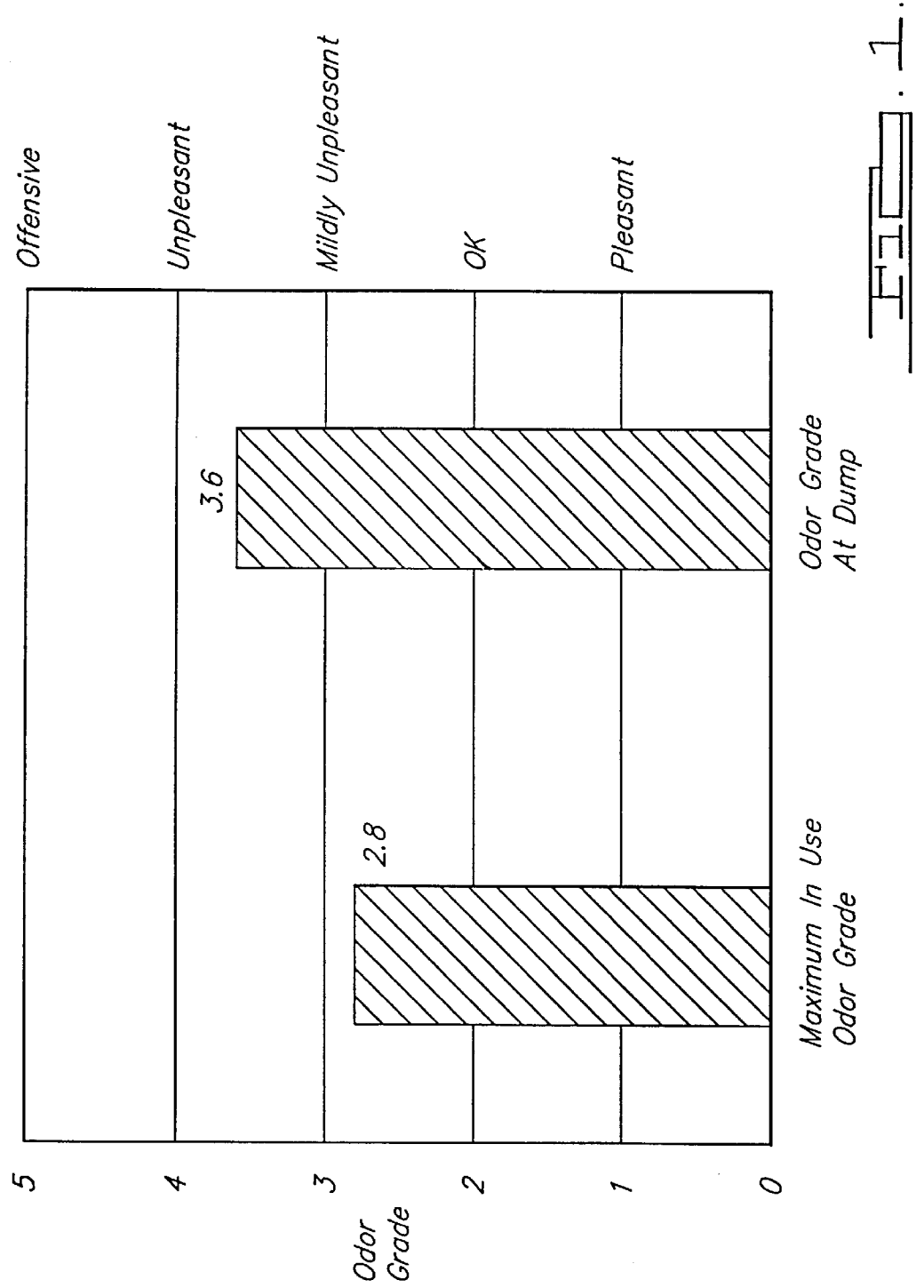

NITRATE DEODORANT COMPOSITION

FIELD OF THE INVENTION

The present invention relates generally to a deodorant composition and more particularly, to a granular nitrate deodorant composition.

BACKGROUND OF THE INVENTION

It is well known in the art to add nitrates or nitrites to sewer systems, municipal waste treatment plants and other industrial waste areas to reduce the level or activity of anaerobic, stench causing bacteria. By reducing the level of anaerobic bacteria, objectional odors such as hydrogen sulfide and mercaptans, are suppressed. Moreover, aerobic bacteria which are important for the sewage treatment process, can use the oxygen from the nitrate to survive and grow.

Although several nitrate-containing deodorant formulations are presently employed in sewage-related settings, some are in powder form which produce dust especially upon use, which may stain surrounding areas. Similarly, other known formulations are in liquid form which, when poured, can splash, also staining surrounding areas. In addition, liquid formulations are relatively heavy and therefore may be cumbersome to use.

It would thus be desirable to provide a nitrate-containing deodorant composition which is relatively easy to use in various sewage-related settings.

SUMMARY OF THE INVENTION

A nitrate containing composition is provided which may be used as a deodorant in sewage-related settings such as waste holding tanks. The composition of the present invention comprises nitrate beads, and a fragrance, wherein the beads are dried with a drying agent to produce dry, free flowing granules. The nitrate beads generally comprise ammonium nitrate, sodium nitrate, potassium nitrate, magnesium nitrate, calcium nitrate, and combinations thereof, as commonly used in fertilizer granules. The granules are relatively easy to use, are lighter than known liquid compositions, and require no preservative or thickening agent.

BRIEF DESCRIPTION OF THE DRAWINGS

The various advantages of the present invention will become apparent to one skilled in the art by reading the following specification and subjoined claims and by referencing the following drawings in which:

FIG. 1 is a bar graph showing the performance of the composition of the present invention.

DETAILED DESCRIPTION OF THE PREFERRED EMBODIMENTS

A nitrate deodorant composition is provided which may be used to deodorize and still enhance biological activity in waste holding tanks and other sewage-related applications. The composition of the present invention comprises nitrate beads, wetted with a fragrance, and dried with a drying agent. The resulting dry granules are free flowing and therefore reduce many of the inconveniences associated with the use of known powder and liquid nitrate formulations.

The nitrate beads used to produce the granules of the present invention are generally fertilizer granules, for example ammonium nitrate available from Soferti. Calcium salpeter 15 available from Norsk Hydro which contains 78% calcium and 6% ammonium nitrate is preferred.

The fragrance employed in the present invention may be any fragrance composition commonly used in the art. It will be appreciated that the amount of fragrance used will be dependent on the type of fragrance composition employed, however, from about 0.5% to about 5% by weight of the total composition, is generally sufficient and from about 0.5% to about 2% is preferred. While not wishing to be bound by theory, it is believed that the fragrance masks any odors produced by the anaerobic bacteria.

The fragrance is applied by wetting the nitrate beads. The wetted beads are then dusted with a drying agent to dry the beads, thereby producing free flowing granules. The drying agent may be chosen from those known in the art such as fumed silica Cab-o-sit® available from Cabot and precipitated silicates such as Ketjen SM 614® available from AKZO Nobel. It will be appreciated that the amount of drying agent employed will be dependent on the wetted beads however from about 0.5% to about 5% by weight of the total composition, is generally sufficient and from about 0.5 to about 3% is preferred.

In an alternative embodiment of the present invention, a surfactant may be also used to wet the beads. Without wishing to be bound by theory, it is believed that the surfactant aids in digesting waste, thereby making it more accessible to the nitrate. The surfactant may be anionic or cationic and nonionic surfactants are preferred such as Emulsin R040® available from Henkel.

Those skilled in the art will readily recognize that the present invention may be employed in various sewage-related settings i.e., where fluid waste is not being drained directly into a sewage system. The present invention is particularly useful for waste holding tanks, for example in portable and mobile lavatories and recreational vehicles. Those skilled in the art will also appreciate that an effective amount of the granules of the present invention may be determined based on the knowledge of one so skilled and the specific application.

The following specific examples further describe the present invention.

SPECIFIC EXAMPLE 1

A particular formulation for a chemical toilet was prepared containing the following ingredients:

| | |
|---|---|
| Calcium salpeter fertilizer beads | 95.75% |
| Etoxylated castor oil | 0.75% |
| Fragrance | 2.0% |
| Precipitated silicate | 1.4% |
| Green dye | 0.1% |

The liquid constituents i.e., the fragrance, the etoxylated castor oil and the dye, were mixed and sprayed onto the calcium salpeter, thus wetting the beads. The mixture was stirred until all the beads were equally wetted. The silicate was then added to produce a homogenous free flowing product.

SPECIFIC EXAMPLE 2

The toilet deodorant described in Specific Example 1 was tested in a Thetford Porta Potti® portable toilet. A dosage of 70 grams of the toilet deodorant was used. In this test the holding tank was heated during the day to challenge the deodorant. The toilet was used by adults for both urinations and defecations to fill the 20 liter holding tank in four days. As shown in FIG. 1, Porta Potti® toilet tests show that the performance was good both during use and at the disposal of the holding tank content.

The foregoing discussion discloses and describes merely exemplary embodiments of the present invention. One skilled in the art will readily recognize from such discussion, and from the accompanying claims, that various changes, modifications and variations can be made therein without departing from the spirit and scope of the invention as defined in the following claims.

We claim:

1. A dry, granular, deodorant composition comprising nitrate beads, wherein the beads comprise a compound selected from the group consisting of sodium nitrate, magnesium nitrate, ammonium nitrate, potassium nitrate, calcium nitrate and combinations thereof, and wherein the beads are wetted with a liquid fragrance and dusted with a drying agent, wherein the drying agent is selected from the group consisting of silica, silicate and combinations thereof.

2. The composition of claim 1, wherein the beads comprise calcium nitrate.

3. The composition claim 1, wherein the drying agent is present in an amount of from about 0.2% to about 5% by weight of the total composition.

4. The composition of claim 1, wherein the fragrance is present in an amount of from about 0.5% to about 5% by weight of the total composition.

5. A method of making dry, deodorant granules comprising the steps of:

a) wetting nitrate beads with a fragrance;

b) applying a drying agent to the beads, wherein the drying agent is selected from the group consisting of silica, silicate and combinations thereof.

6. The method of claim 5, wherein the nitrate beads comprise a compound selected from the group consisting of sodium nitrate, ammonium nitrate, potassium nitrate, calcium nitrate, and combinations thereof.

7. The method of claim 5, wherein the nitrate beads are further wetted with a surfactant.

8. The method of claim 5, wherein the drying agent is present in an amount of from about 0.2% to about 5% by weight of the total composition.

9. The method of claim 5, wherein the fragrance is present in an amount of from about 0.5% to about 5% by weight to the total composition.

* * * * *